(12) United States Patent
Agarelli et al.

(10) Patent No.: US 8,410,036 B2
(45) Date of Patent: Apr. 2, 2013

(54) COMPOSITION FOR PERMANENT OR SEMIPERMANENT TINTING OF KERATIN FIBERS WITH OIL-IN-GLYCOL LAMELLAR GEL

(75) Inventors: Alexandra Bazito Agarelli, Sao Paulo (BR); Nelson Luis Perassinoto, Campinas (BR); Maria Regina Bartuccio Raponi, Sao Caetano Do Sul (BR); Ligia Vairoletto, San Paulo (BR); Liliana Calore Brenner, Sao Paulo (BR)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 13/442,421

(22) Filed: Apr. 9, 2012

(65) Prior Publication Data

US 2012/0255130 A1 Oct. 11, 2012

Related U.S. Application Data

(63) Continuation of application No. 12/528,674, filed as application No. PCT/US2008/054943 on Feb. 26, 2008, now Pat. No. 8,153,571.

(30) Foreign Application Priority Data

Feb. 27, 2007 (BR) .................................... 0705069

(51) Int. Cl.
*C11D 1/835* (2006.01)
*C11D 3/44* (2006.01)

(52) U.S. Cl. ........ 510/119; 510/130; 510/182; 510/340; 510/341; 510/342; 510/343; 510/356; 510/358; 510/384; 510/432; 510/433; 510/504

(58) Field of Classification Search ................... 510/130, 510/182, 340, 341, 342, 343, 356, 358, 384, 510/432, 433, 504, 119
See application file for complete search history.

(56) References Cited

U.S. PATENT DOCUMENTS

| | | | |
|---|---|---|---|
| 6,596,035 B2 | 7/2003 | Gutkowski et al. | |
| 6,733,541 B2 | 5/2004 | Pratt | |
| 2003/0108502 A1* | 6/2003 | Uchida et al. | 424/70.11 |
| 2003/0135935 A1 | 7/2003 | Yang et al. | |
| 2003/0180278 A1* | 9/2003 | Hoppe et al. | 424/94.1 |
| 2005/0180941 A1* | 8/2005 | Doi et al. | 424/70.27 |
| 2005/0196367 A1 | 9/2005 | Ohta et al. | |
| 2005/0283925 A1 | 12/2005 | Glenn et al. | |
| 2006/0078527 A1* | 4/2006 | Midha et al. | 424/70.27 |
| 2007/0172441 A1* | 7/2007 | Takeda et al. | 424/70.13 |
| 2008/0115297 A1* | 5/2008 | Bolton et al. | 8/408 |
| 2008/0131469 A1* | 6/2008 | Hashimoto | 424/401 |
| 2009/0068134 A1* | 3/2009 | Kaharu | 424/70.1 |
| 2009/0142381 A1* | 6/2009 | Agarelli et al. | 424/401 |

* cited by examiner

*Primary Examiner* — Charles Boyer
(74) *Attorney, Agent, or Firm* — William J. Davis; Thompson Hine LLP

(57) ABSTRACT

The present application is directed to an oil-in-glycol lamellar gel, which comprises (a) at least one glycol, (b) at least one fatty alcohol, (c) at least one cationic surfactant, (d) at least one non-ionic surfactant and (e) at least one amino acid, for application as an addictive for permanent or semi-permanent keratin fiber color products, being the said lamellar gel able to improve dispersion of colorant agents in the color composition and the distribution, diffusion, interaction and maintenance of the colorant agents in the keratin fibers, which results in greater color vitality and retardation of the discoloring process.

24 Claims, 5 Drawing Sheets

COMPOSITION FOR PERMANENT OR SEMIPERMANENT TINTING OF KERATIN FIBERS WITH OIL-IN-GLYCOL LAMELLAR GEL

FIELD OF THE INVENTION

The present invention has for object an oil-in-glycol lamellar gel, which comprises (a) at least one glycol, (b) at least one fatty alcohol, (c) at least one cationic surfactant, (d) at least one non-ionic surfactant and (e) at least one amino acid, for application as an addictive for permanent or semi-permanent keratin fiber color products, being the said lamellar gel able to improve dispersion of colorant agents in the color composition and the distribution, diffusion, interaction and maintenance of the colorant agents in the keratin fibers, which results in greater color vitality and retardation of the discoloring process.

BACKGROUND ART

The keratin fibers are filiform structures comprised of keratin cells produced by the hair follicle, which has color, variable structural and morphological characteristics according to their location and age, which can include hair and body hair in general, eyebrows, eyelashes, moustache, beard and other human being or animal hair, or synthetic substrates.

Human hair, for instance, has a complex structure that consists of three different morphological components, and keratin is the primary element, which corresponds to at least 65% of the keratin fiber. The central portion of the fiber is known as medulla. It is surrounded by the cortex, which is a layer composed of keratin cells that provide mechanic force to the entire fiber. The outermost layer is the cuticle, a thin layer of overlaid keratin scales, which serves as a protective barrier.

The natural color of these fibers derives from the pigment particles that are produced in the melanocytes and transferred to the cortex and medulla cells. The natural variations, oxidation degree, amount and distribution of these natural pigments along the fiber cause the various hues. The natural color of the human hair, for example, is mainly the result of two types of pigments: eumelanin (black) and pheomelanin (red).

Due to the intrinsic human desire to improve his/her appearance, a number of products designed to change the natural color of the keratin fibers are available in the market. The most common and utilized are the semi-permanent and permanent fiber coloring products.

The semi-permanent or deposition fiber coloring products, also known as tonalizers, include products that are capable of changing the natural color of the keratin fibers to some extent, being gradually washed away at every wash. These products must be ready to use and easy to apply and include low molecular weight and high keratin affinity coloring agents in their formula, for instance, those of the nitro-family, as well as the nitroanilines, nitrophenylenediamines and nitroaminophenol derivatives, which penetrate into the cuticle and partially into the fiber cortex, which results in an average resistance from 5 to 12 washes.

The choice between the coloring agents is a big barrier against the formulation of this type of product, because the affinity of these agents along the different portions of the fiber length is not homogeneous, i.e., certain compounds have affinity for these more damaged regions (tip-ends) while others for less damaged regions (root).

Permanent fiber coloring products, also called oxidant fiber coloring products, are the only ones that can provide long lasting color, with the options for many tonalities and more extensive cover to the fibers.

In the permanent tinting process, the original color of the fiber shall be made unnatural so as to form afterwards a new color by means of oxidative condensation. In order for permanent color fixation to occur, the reaction that forms the coloring agent must occur in contact with the keratin fiber. For this purpose, the permanent fiber color products are divided in a first composition, which contains the coupling basis (coloring agents) and an alkaline agent and a second composition containing the oxidant agent, usually hydrogen peroxide.

The coupling basis consists of dye primary intermediates, which are modified during the reaction of oxidation, developing the colors. This category includes the aromatic diamines, aminophenols and diaminophenols. These intermediates are the key to create basic hues as well as to cover dispigmented fibers.

The couplers or modifiers are responsible for the colors themselves. Separately they only produce weak colors, but when reacted with the bases, in presence of an oxidant agent, in alkaline medium, they modify the colors of the bases, generating new colors to the keratin fibers. The most employed modifiers are m-diamine, m-aminophenol and polyphenols. Some heterocyclic derivatives are used as couplers, in order to increase the durability of the fiber coloring products and avoid discoloration after a number of washes, for example, 6-hidroxindol and 2-amino-3-hidroxipiridine.

When the two phases are mixed, an oxi-reduction occurs and leads to the formation of the color itself. Simultaneously, part of the hydrogen peroxide will dissolve the natural pigment of the fiber that is being attacked by the alkaline agent, usually ammonia or monoethanolamine. The solubilization of the natural pigment will cause this latter to be replaced by the color agent that is forming during the oxi-reduction reaction, generating the new color.

Various external factors can provoke the degradation of the colors obtained by semi-permanent or permanent fiber coloring products, for example, light, heat, pollution, water hardness, UV radiation, etc. In the case of permanent fiber coloring products, these factors can be worsened if there is excess of couplers, which might generate excess of undesirable byproducts. Other influent factor is the reaction speed, for the oxidation process must be controlled so as to take place inside the cuticle of the keratin fiber in order to, in a certain period of time, complete the reaction. When the reaction occurs in less time than required, the formed coloring agent will be located in the external region of the keratin fiber and will be washed away and when it is superior to the required, the reaction will not be completed at the process end. In this sense, an important aspect is the permeation of the coloring agents and their spread along the keratin fibers.

The appropriate carrier for these products can include solution, liquid, emulsion, pseudo-emulsion, oil that converts into gel, gel, shampoo or powder, being barrier, in some cases, the complete dispersion of the coloring agents in these mediums.

To solve the above-mentioned problems, the fiber coloring compositions usually count only on the coloring agent characteristics. Some compositions had cationic and/or amphoteric compounds added to them, which are quaternary or polyquaternary, etc., as exemplified in the patents FR 2402446, FR2428438, FR2687570 and U.S. Pat. No. 3,986, 825, which allow more vibrant colors and less tendency to lose color, but they do not interfere with the diffusion of the coloring agents nor swelling of the capillary fiber nor homogeneity of the color.

Thus, it is desired improvements regarding the manufacturing process of semi-permanent and permanent coloring products for keratin fibers and concerning the attributes and quality of these products.

DESCRIPTION OF THE INVENTION

Figure 1:
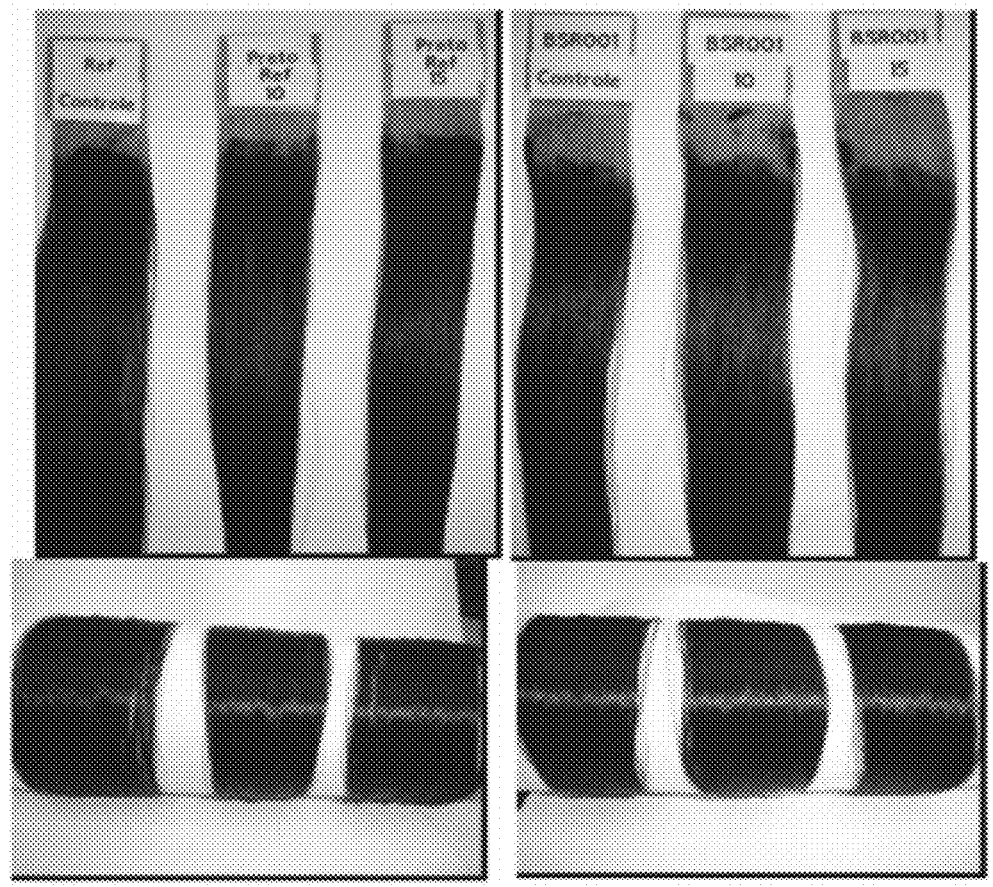
FIGS. 1-5 are comparative images of hair tufts with and without an oil-in-gel lamellar gel in accordance with Example 1 both before and after washing with sodium lauryl sulfate (SLES) as explained in more detail in Example 2.

The dispersion of the coloring agents in the coloring products composition, as well as its distribution, diffusion, interaction and maintenance in the keratin fibers, resulting in greater color vitality and retarding of discoloration, can be particularly improved when these agents are formulated with a oil-in-glycol lamellar gel system according to the present invention.

Furthermore, the employment of the lamellar gel helps simultaneously improve the general characteristics of the hair, like conditioning, combing and texture.

Firstly, the present invention is about an oil-in-glycol lamellar gel that comprises (a) at least one glycol, (b) at least on fatty alcohol, (c) at least one cationic surfactant, (d) at least one non-ionic surfactant and (e) at least one amino acid.

The glycols used in the lamellar gel of the present invention are those which have at least two hydroxyls, like the butylene glycol or propylene glycol, particularly those which have three hydroxyls, like the 1,2,3-propanotriol. The amount of glycol in the lamellar gel can vary between about 40 to about 90%, preferably between about 50% and about 80%, more particularly between about 65% and about 75% in weight, based on the total weight of the lamellar gel.

The fatty alcohols that are used in the lamellar gel described herein comprise $RCH_2OH$ compounds, wherein R denotes saturated or unsaturated hydrocarbon radical having from 5 to 27 in average, preferably from 10 to 22 atoms of carbon, in a linear or branched chain.

Appropriate fatty alcohols according to the present invention can be selected from cetyl, isocetyl, stearyl, isostearyl, behenic, oleic, linoleic and/or cetearyl alcohols. Fatty alcohols can be used individually or in the form of mixtures.

An appropriate amount of fatty alcohol in the lamellar gel of the present invention ranges from about 0.1 to about 40%, preferably between about 3 to about 35% and more preferably between about 5 to about 10% in weight, based on the lamellar gel total weight.

Cationic surfactants that are useful to the present invention can be all those that can form a lamellar gel structure, particularly quaternized surfactants. The preferable quaternized surfactants according to the present invention are the quaternary compounds of ammonium with general formula $(R, R', R'', R''' N)^+ X^-$, where R, R', R'' and R''' are similar or different and where $X^-$ represents an anion, for example, chloride. The R group can be aliphatic or carry additional substitutionals and N can be part of a heterocyclic or aromatic ring.

In the most preferable quaternized surfactants, R and R' are $CH_3$, and R'' and R''' are aliphatic or aromatic chains, for example cetearyl-amido-propyl-dimonium hydroxyethyl chloride, dimethylpabamidopropyl laurdimonium tosylate, quaternium 70, or mixtures thereof.

An appropriate amount of cationic surfactant in the lamellar gel of the present invention ranges from about 0.001 to about 30%, preferably between about 0.01 to about 25% and most preferably between about 0.2 to about 20% in weight, based on the lamellar gel total weight.

The non-ionic surfactant, according to the present invention, is an alkyl pyrrolidone, particularly a lauryl pyrrolidone, and its amount can range from about 0.1 to about 20%, particularly between about 5 to about 15%, more particularly between about 9 to about 11% in weight in relation to the lamellar gel total weight.

The amino acid can be selected from among glycine, lauroyl lysine, arginine HCL, n-acetyl cysteine or their mixtures and their quantities in the lamellar gel composition in accordance with the present invention can range from about 0.1 to about 5%, particularly between about 0.5 to about 1.5% in weight in relation to the total weight of the composition.

The lamellar gel of the present invention is, preferably, substantially water free, i.e., it can comprise a small amount of water provided that its profile is not substantially altered.

Other object of the present invention is a process of preparation of a oil-in-glycol lamellar gel, which consists of (1) heating separately at least one glycol, at least one cationic surface-active agent and at least one fatty alcohol up to a temperature of from about 65° C. to about 85° C., particularly between about 70° C. to about 75° C.; (2) mixing the heated components in the previous step under agitation; (3) keeping the agitation until homogenization is reached; (4) cooling down the homogenized mixture from about 30° C. to about 50° C., particularly up to 40° C.; (5) adding at least one non-ionic surfactant and (6) adding at least one amino acid.

Other object of the present invention is the use of the oil-in-glycol lamellar gel to prepare a composition for tinting keratin fibers and a process for preparation of the said composition.

The process consists of pre-dispensing all or part of the coloring agents that will be employed in the oil-in-glycol lamellar gel coloring composition according to the present invention, particularly in 1:1 proportion. the amount of coloring agents in a fiber coloring composition can range from about 0.5 to about 5% in weight, therefore, the amount of lamellar gel employed in the pre-dispersion of these agents can also range from about 0.5 to about 5% in weight, being that the limiting factor, is the complete dissolution of the coloring agents in the lamellar gel.

One can understand by coloring agents in the present invention, all the compounds that direct or indirectly give color to the keratin fibers, whether they are pigments or direct or indirect hair coloring products or their intermediaries.

In other aspect, the present invention is about a composition for tinting keratin fibers that comprises the oil-in-glycol lamellar gel according to the present invention and cosmetically acceptable excipients. Without any limitations, the excipients can include those mentioned in the "Handbook of Food Drug and Cosmetic Excipients", Florida: CRC Press, 2000.

The fiber coloring compositions according to the present invention include, without restriction, solution, liquid, emulsion, pseudo-emulsion, gel-convertible oil, gel, shampoo or powder, with particular preference for emulsions.

The technical advantages mentioned herein, without limiting the present invention to the any technical explanation, are due to the fact that the lamellar gel according to the present invention to regulate the reaction of oxidation through the presence of its non-ionic surface-active agent, which resonates and balances the byproducts elaborated in the oxidative processes, consequently the color of the coloring agent. Furthermore, the oil-in-glycol lamellar gel according to the present invention provides greater affinity of the coloring agents to the keratin fibers, through the formation of anioniccationic complexes of the lamellar gel and keratin fiber system itself, especially when they are damaged.

Furthermore, the lamellar gel medium has weaker polarity than the water medium, which, in contact with the coloring agents, cause them to spread out more evenly, interact easier with the fibers and wear less after wash.

The lamellar gel according to the present invention also causes the fusion point of all the system components to drop, or, in consequence, causes the glass transition point to drop of about 10° C., combining the advantages of a gel and a cream at the same time, although there is only one additive for pre-dispersion of the coloring agents.

Another object of the present invention is a cosmetic process for coloring the keratin fiber, prepared in any kind of shop that involves any esthetics and/or cosmetics activity, which consists of applying onto them an efficacious amount of a fiber coloring product that comprises the oil-in-glycol lamellar gel according to the present invention.

The following examples serve to illustrate aspects of the present invention without any restricting character. Application to the hair is mentioned only for simplicity of presentation, without being limited to this use.

EXAMPLES

Example 1

Process of Preparation 69 g of 1,2,3-propanotriol were heated in a first recipient until 75° C.

In a second recipient 20 g of a mixture of behenic alcohol, cetearyl alcohol, isostearyl alcohol and hydroxyethyl chloride cetearyl-amide-propyl-dimonium were heated until 70° C., which was added to the first recipient while being agitated.

The agitation was kept and the new solution was cooled down until 40° C. Next 10 g of lauryl pyrrolidone and 1 g of glycine were added under agitation, terminating the process.

Example 2

Study of the Functional Properties of the Lamellar Gel in Example 1 Effect of the Oil-In-Gel Lamellar Gel in Color Intensity and Homogeneity and its Resistence to Sles Washes Hair coloring products containing many families of coloring agents with (BSR001) and without (control) oil-in-gel lamellar gel of the example 1 in their compositions were applied in Caucasian standard-type hair tufts, discolored 1 or 2 times according to the lab market methodology. Next, the tufts were washed 10 to 15 times with sodium lauryl ether sulfate (SLES). The procedure was applied to check the interference of the lamellar gel in the characteristics concerning the initial quality and post-wash for comparison, revealing that in the three different families of pigments utilized, the lamellar gel served to intensify the tonality of the color, improve the distribution of the pigments and the maintenance of the color after the wash with SLES in all the pigment families.

In all these tests, the lamellar gel was used in 1:1 proportion.

Figure 2:
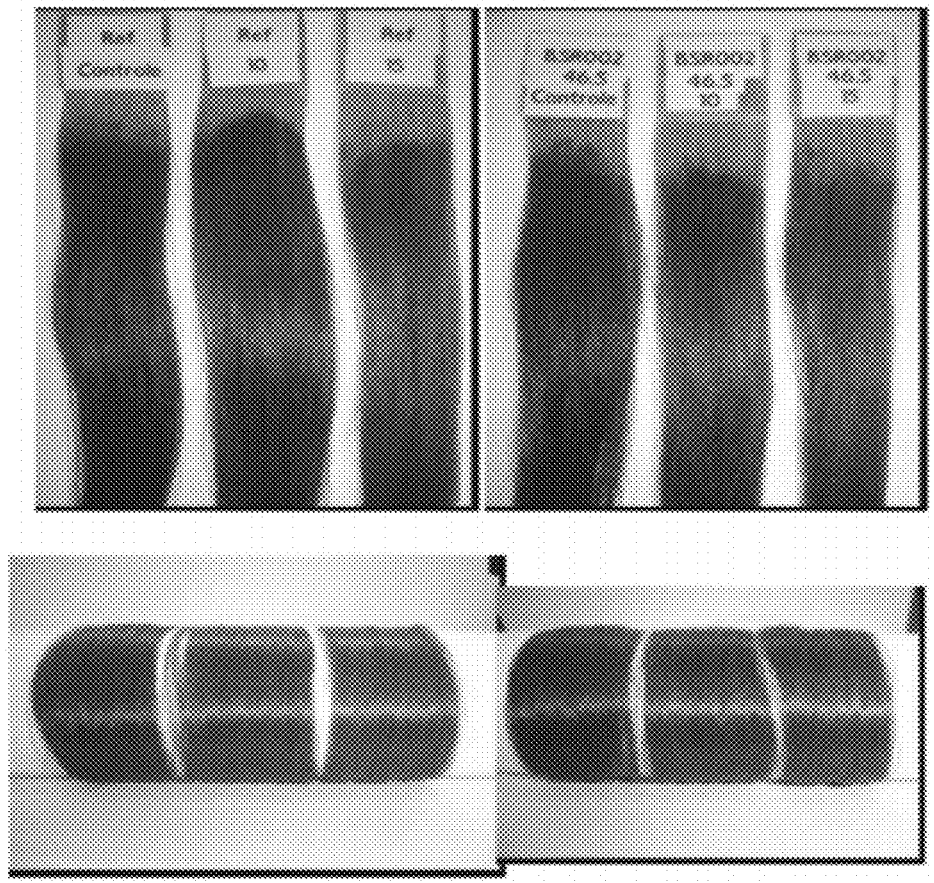
Figure 3:
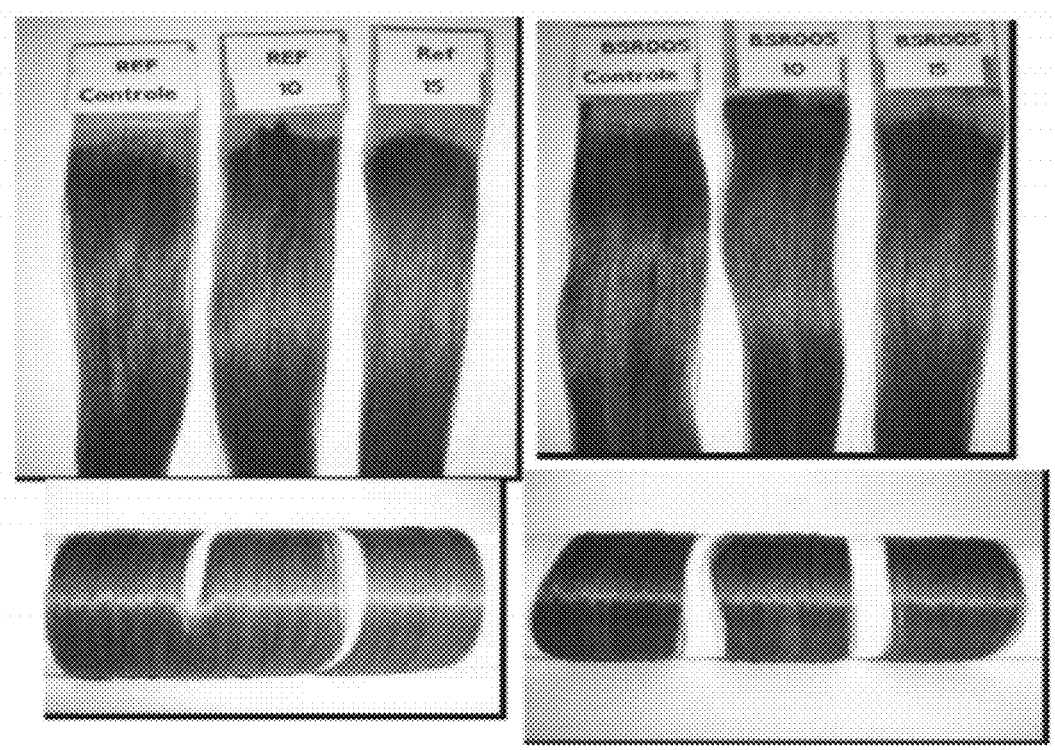

We can observe through the comparative images of the FIGS. 1 to 3, which, for all the evaluated groups, there was an improvement in coloring power for all the samples that contained the lamellar gel according to the present invention. Being this improvement relative to the initial coloring power, causing color to be more vibrant as well as maintaining the color after 10 to 15 washes in relation to the benchmark samples without the lamellar gel.

Figure 4:
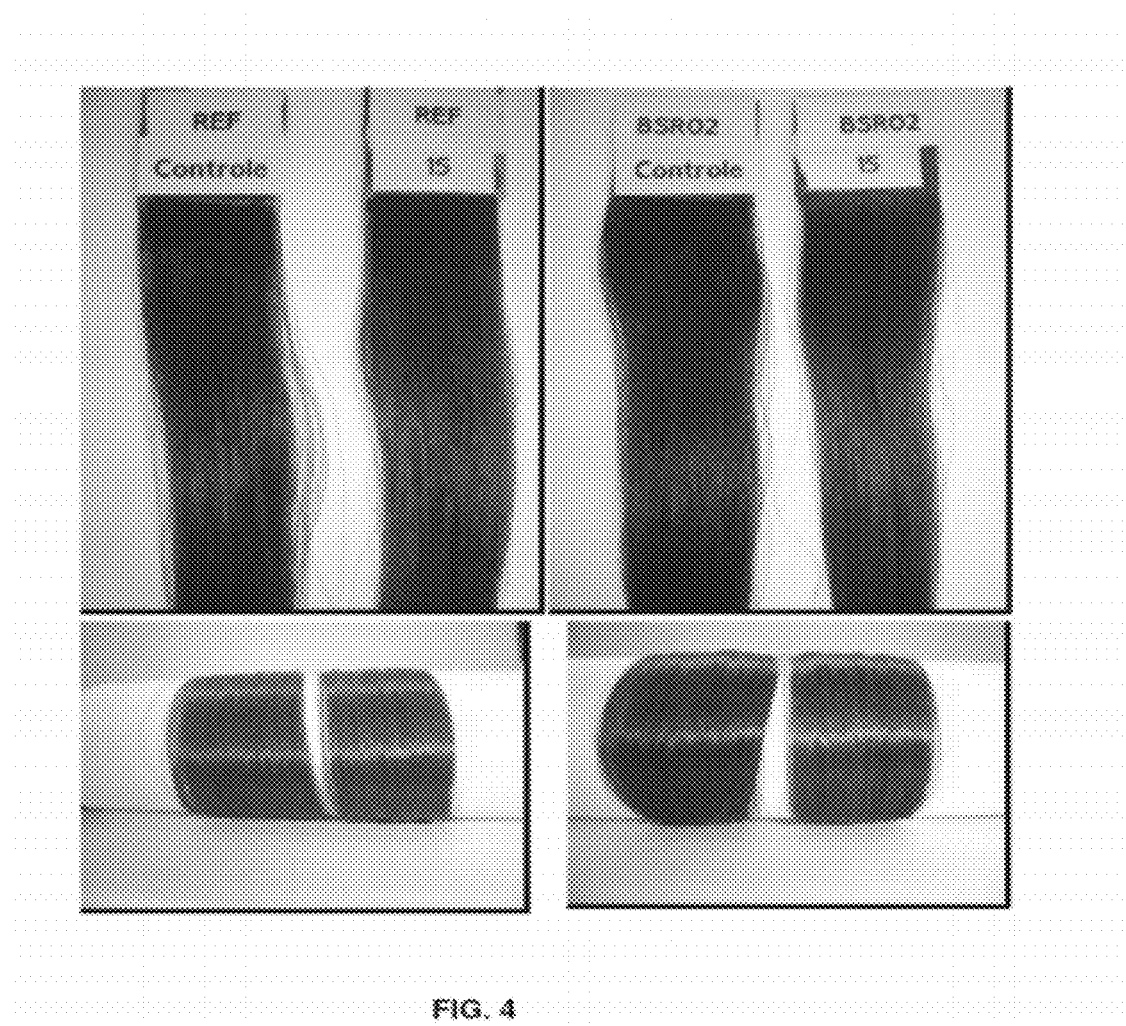
Figure 5:
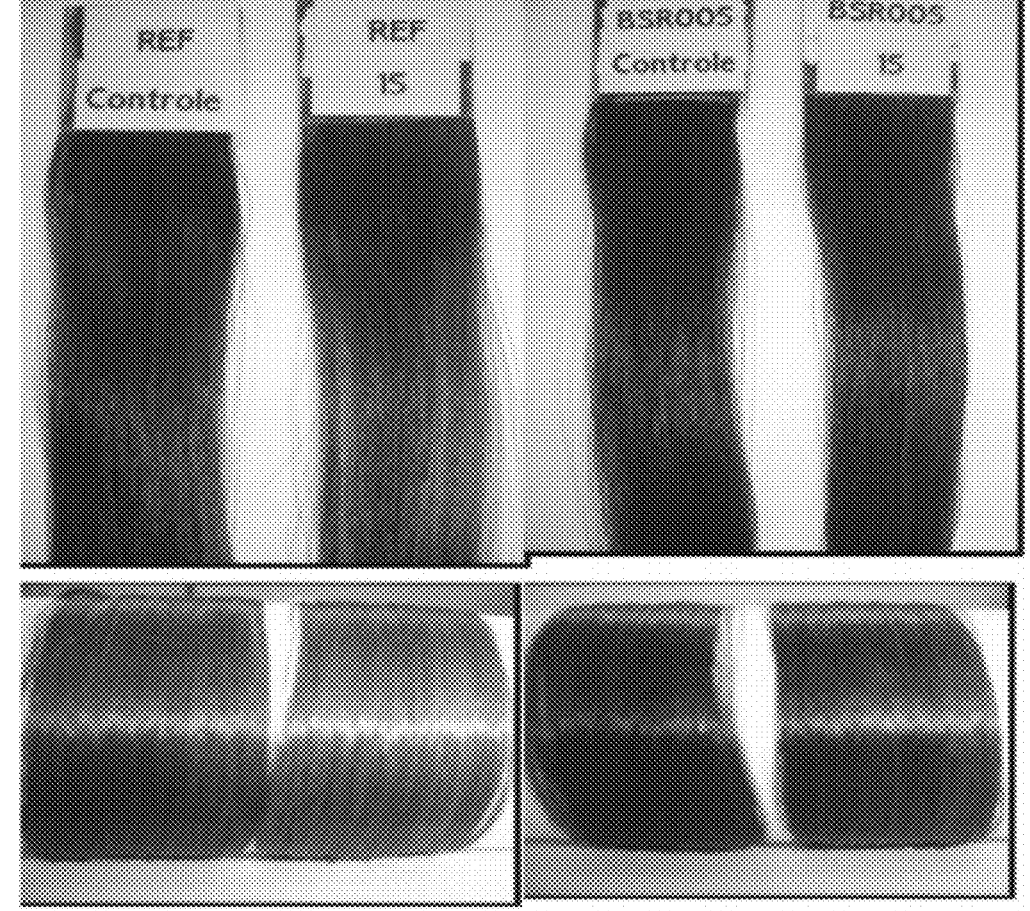

Even with the inclusion of greater percentage of damage to the fiber, due to 2 previous processes of discoloration at high temperature, we can observe through the comparative images of the FIGS. 4 to 5, that for all the evaluated groups, a better coloring power improvement was achieved for all the samples that had the oil-in-glycol lamellar gel (BSR005). Being this improvement relative to the initial coloring power, causing color to be more vibrant color as well as maintaining the color after 15 washes in relation to the benchmark samples without the lamellar gel.

What is claimed is:

1. OIL-IN-GLYCOL LAMELLAR GEL comprising (a) at least one glycol selected from the group consisting of butylene glycol, propylene glycol, 1,2,3-propanetriol and mixtures thereof, (b) at least one fatty alcohol, (c) at least one cationic surfactant, (d) at least one non-ionic surfactant and (e) at least one amino acid selected from the group consisting of glycine, lauroyl lysine, arginine HCL, n-acetyl cysteine, and mixtures thereof; wherein the amount of glycol ranges from about 40 to about 90% in weight in relation to the total weight of the composition.

2. OIL-IN-GLYCOL LAMELLAR GEL, according to claim 1, characterized by the fact that the amount of glycol ranges from about 50% to about 80% in weight in relation to the total weight of the composition.

3. OIL-IN-GLYCOL LAMELLAR GEL, according to claim 2, characterized by the fact that the amount of glycol ranges from about 65% to about 75% in weight in relation to the total weight of the composition.

4. OIL-IN-GLYCOL LAMELLAR GEL, according to claim 1, characterized by the fact that the fatty alcohol is selected from those which have the generic formula $RCH_2OH$, where R represents a saturated or unsaturated hydrocarbon radical with 5 to 27 atoms of carbon in average, and the linear or branched chain hydrocarbon radical.

5. OIL-IN-GLYCOL LAMELLAR GEL, according to claim 4, characterized by the fact that the fatty alcohol is selected from the group consisting of cetylic, isocetyl, stearyl, isostearyl, behenic, oleic, linoleic, cetearyl alcohols and mixtures thereof.

6. OIL-IN-GLYCOL LAMELLAR GEL, according to claim 1, characterized by the fact that the amount of fatty alcohols ranges from about 0.1 to about 40% in weight in relation to the total weight of the composition.

7. OIL-IN-GLYCOL LAMELLAR GEL, according to claim 6, characterized by the fact that the amount of fatty alcohol ranges from about 3 to about 35% in weight in relation to the total weight of the composition.

8. OIL-IN-GLYCOL LAMELLAR GEL, according to claim 7, characterized by the fact that the amount of fatty alcohol ranges from about 5 to about 10% in weight in relation to the total weight of the composition.

9. OIL-IN-GLYCOL LAMELLAR GEL, according to claim 1, characterized by the fact that the cationic surfactant is one or more quaternized surface-active agents selected from the quaternary compounds of ammonium of general formula $(R, R', R'', R'''N)^+X^-$, where R, R', R'' and R''' can be identical or different, aliphatic or carry extra substitutionals, $X^-$ represents an anion and N is part of the heterocyclic or aromatic ring.

10. OIL-IN-GLYCOL LAMELLAR GEL, according to claim 9, characterized by the fact that the quaternized cationic surfactant is selected from the group consisting of cetearylamido-propyl-dimonium hydroxyethyl chloride, dimethylpabamidopropyl laurdimonium tosylate, quaternium 70 and mixtures thereof 11. OIL-IN-GLYCOL LAMELLAR GEL, according to claim 1, characterized by the fact that the amount of cationic surfactant ranges within about 0.001 and about 30% in weight in relation to the total weight of the composition.

12. OIL-IN-GLYCOL LAMELLAR GEL, according to claim 11, characterized by the fact that the amount of cationic surfactant ranges from about 0.01 to about 25% in weight in relation to the total weight of the composition.

13. OIL-IN-GLYCOL LAMELLAR GEL, according to claim 12, characterized by the fact that the amount of cationic surfactant ranges from about 0.2 to 20% in weight in relation to the total weight of the composition.

14. OIL-IN-GLYCOL LAMELLAR GEL, according to claim 1, characterized by the fact that the amount of non-ionic surfactant ranges from about 0.1 to about 20% in weight in relation to the total weight of the composition.

15. OIL-IN-GLYCOL LAMELLAR GEL, according to claim 14, characterized by the fact that the amount of non-ionic surfactant ranges from about 5 to about 15% in weight in relation to the total weight of the composition.

16. OIL-IN-GLYCOL LAMELLAR GEL, according to claim 15, characterized by the fact that the amount of non-ionic surface-active agent ranges from about 9 to about 11% in weight in relation to the total weight of the composition.

17. OIL-IN-GLYCOL LAMELLAR GEL, according to claim 1, characterized by the fact that the amount of amino acid ranges from about 0.1 to about 5% in weight in relation to the total weight of the composition.

18. OIL-IN-GLYCOL LAMELLAR GEL, according to claim 17, characterized by the fact that the amount of amino acid ranges from about 0.5 to about 1.5% in weight in relation to the total weight of the composition.

19. PROCESS FOR PREPARATION OF OIL-IN-GLYCOL LAMELLAR GEL in accordance with claim 1 comprising: (1) heating separately at least one glycol, at least one cationic surfactant and at least one fatty alcohol up to a temperature of about 65° C. to about 85° C.; (2) mixing under agitation the components heated in the previous step; (3) maintaining the agitation until homogenization; (4) cooling down the homogenized mixture between about 30° C. and about 50° C.; (5) adding at least one non-ionic surfactant and (6) adding at least one amino acid to form an oil-in-glycol lamellar gel.

20. PROCESS, according to claim 19, characterized by the fact that the temperature of step (1) ranges from about 70° C. to about 75° C.

21. PROCESS, according to claim 19, characterized by the fact that the temperature of step (4) is about 40° C.

22. PROCESS FOR MANUFACTURING OF A COMPOSITION FOR PERMANENT OR SEMI-PERMANENT TINTING OF KERATIN FIBERS characterized by the fact that it comprises pre-dispersing all or part of coloring agents of a coloring composition in the oil-in-glycol lamellar gel according to claim 1.

23. PROCESS, according to claim 22, characterized by the fact that the proportion between the coloring agents of the fiber coloring composition and the oil-in-glycol lamellar gel is 1:1.

24. COSMETIC PROCESS FOR TINTING OF KERATIN FIBERS, characterized by the fact that it comprises applying an efficacious amount of a fiber coloring composition to keratin fibers wherein the fiber coloring composition comprises the oil-in-glycol lamellar gel according to claim 1.

* * * * *